United States Patent [19]

Wilk et al.

[11] Patent Number: 5,314,803
[45] Date of Patent: * May 24, 1994

[54] PROCESS AND TEST CARRIER FOR THE DETERMINATION OF AN ENZYME FROM AN ISOENZYME MIXTURE

[75] Inventors: Hans-Erich Wilk; Anselm Rothe; Erich Schneider, all of Mannheim, Fed. Rep. of Germany

[73] Assignee: Boehringer Mannheim GmbH, Mannheim, Fed. Rep. of Germany

[*] Notice: The portion of the term of this patent subsequent to Dec. 1, 2008 has been disclaimed.

[21] Appl. No.: 989,875

[22] Filed: Dec. 10, 1992

Related U.S. Application Data

[63] Continuation of Ser. No. 473,007, Jan. 31, 1990, abandoned.

[30] Foreign Application Priority Data

Feb. 2, 1989 [DE] Fed. Rep. of Germany ....... 3903114

[51] Int. Cl.$^5$ .................. C12Q 1/25; C12Q 1/40; G01N 33/573; G01N 21/00
[52] U.S. Cl. ........................ 435/7.4; 435/22; 435/7.1; 435/962; 435/969; 435/970; 422/56; 422/58; 422/61; 422/68.1; 436/63
[58] Field of Search ............. 435/970, 969, 963, 962, 435/22

[56] References Cited

U.S. PATENT DOCUMENTS

| 4,312,834 | 1/1982 | Vogel et al. | 422/56 |
| 4,452,887 | 6/1984 | Kitajima et al. | 435/14 |
| 4,477,575 | 10/1984 | Vogel et al. | 436/170 |
| 4,891,313 | 1/1990 | Berger et al. | 436/7 |
| 4,939,082 | 7/1990 | Naujoks et al. | 435/7 |
| 4,945,043 | 7/1990 | Gerber | 435/7.4 |
| 5,071,746 | 12/1991 | Wilk et al. | 435/7.94 |
| 5,162,238 | 11/1992 | Eikmeier et al. | 436/532 |

FOREIGN PATENT DOCUMENTS

| 1276106 | 11/1990 | Canada | G01N 33/577 |
| 1277231 | 12/1990 | Canada | G01N 33/573 |
| 194502 | 9/1986 | European Pat. Off. | G01N 33/48 |
| 196731 | 10/1986 | European Pat. Off. | G01N 33/48 |
| 209154 | 1/1987 | European Pat. Off. | C12Q 1/40 |
| 293649 | 12/1988 | European Pat. Off. | |

OTHER PUBLICATIONS

Clin. Chem. (1985) vol. 31, No. 8, pp. 1283–1288.
Clin. Chem. (1982) 28:1525–1527.
Clin. Chem. (1985) 31:1000.
Clin. Chem. (1986) 32:1130.
Z. Anal. Chem. (1986) 324:304–305.

*Primary Examiner*—Keith Baker
*Assistant Examiner*—G. Bugaisky
*Attorney, Agent, or Firm*—Felfe & Lynch

[57] ABSTRACT

The present invention provides a process for the determination of an enzyme from an isoenzyme mixture in a liquid sample by inhibition of the disturbing isoenzymes and determination of the non-inhibited enzyme, wherein the isoenzyme mixture is contacted with one or more substances which are able to inhibit the disturbing isoenzymes, the sample containing the inhibiting substance(s) is transferred to a small-pored reaction medium and the disturbing enzyme is there inhibited and the determination of the non-inhibited enzyme is carried out in the resulting liquid.

The present invention also provides a test carrier for carrying out this process.

20 Claims, 2 Drawing Sheets

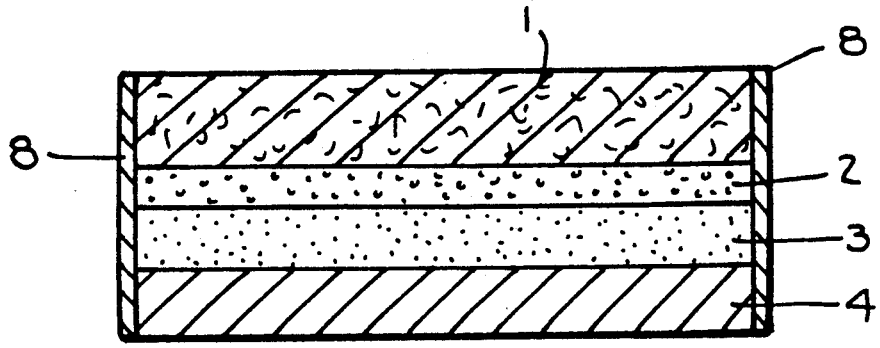
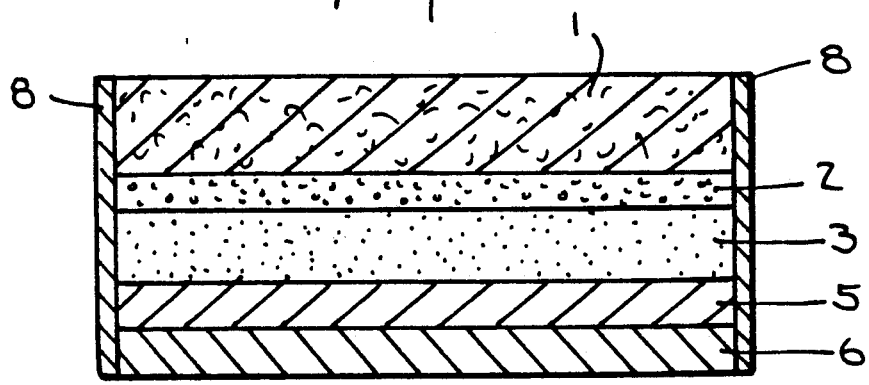
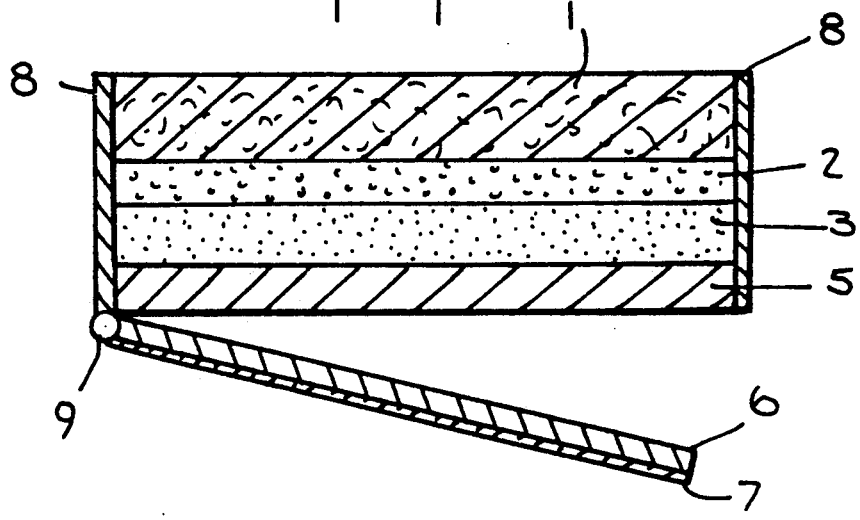

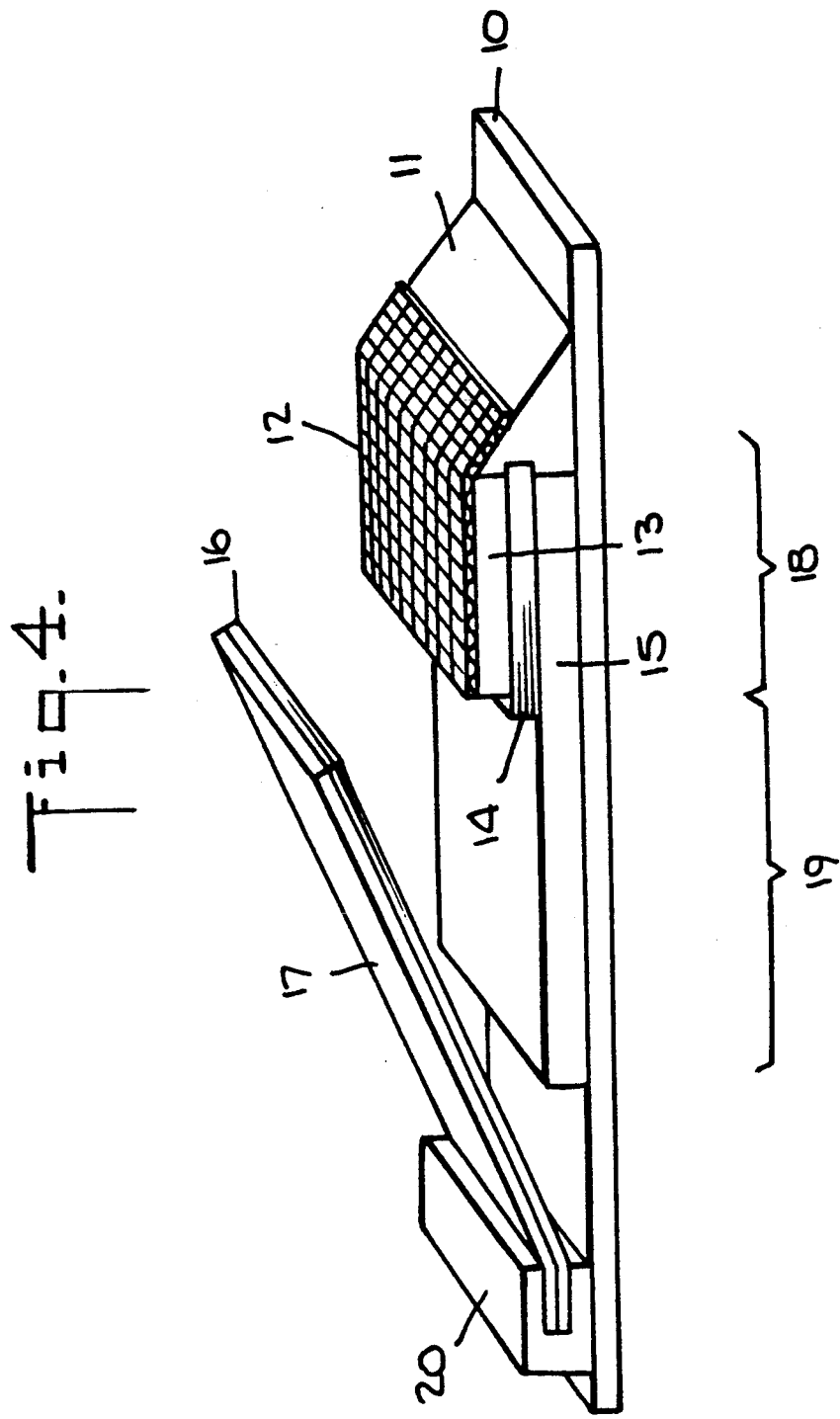

PROCESS AND TEST CARRIER FOR THE DETERMINATION OF AN ENZYME FROM AN ISOENZYME MIXTURE

This application is a continuation of application Ser. No. 07/473,007 filed Jan. 31, 1990 abandoned.

The present invention is concerned with a process for the determination of an enzyme from an isoenzyme mixture in a liquid sample by inhibition of the disturbing isoenzymes and determination of the non-inhibited enzyme.

The present invention also provides a test carrier for the rapid determination of an enzyme from an isoenzyme mixture in a liquid sample by inhibition of the disturbing isoenzymes and determination of the non-inhibited enzyme, which test carrier contains a sample application region and evaluation region, as well as several test layers.

Furthermore, the present invention is concerned with the use of a test carrier for the determination of an enzyme from an isoenzyme mixture in a liquid sample.

The determination of enzyme activities is an important field in medical diagnosis. Thus, for example, the determination of the activity of particular enzymes in body fluids, such as blood, serum, plasma, urine, liquor, saliva or duodenal juice serves for the assessment of whether a disease is present or not. Examples therefor include lactate dehydrogenase (LDH), creatine kinase (CK) and amylase. Also determinations of liquid component materials which are themselves not enzymes are often carried out by means of reactions in which finally an enzyme activity is also measured which represents a measure for the concentration of the component material to be determined. Such substances can be determined by a combination of chemical and enzymatic reactions or by enzymatic reactions alone. Immunological determinations also often involve an enzyme activity determination. Examples therefor include, for example, the so-called enzyme immuno assays (EIA) in which enzymes are used for labelling substances and the measured activity of which finally represents a measure for the substance concentration to be determined. Alkaline phosphatase, galactosidase and peroxidase are often used as labelling enzymes.

A problem in the case of enzyme determinations are false or non-informative measurements due to falsifying isoenzymes. Isoenzymes are to be understood to be enzymes which react with the same substrate to give the same product but which display a different primary structure (amino acid sequence) and/or a different conformation. Such enzymes can originate from the same or different source but they can also be of different origin.

For the recognition of diseases of organs, use is often made of the knowledge that organ-specific enzymes from different organs pass into body fluids. In the case of diseases of an organ, the organ-specific enzymes usually occurring in body fluids, for example blood, plasma, serum, urine, liquor, saliva or duodenal juice, can be present in concentrations different from the normal measurement. However, isoenzymes frequently falsify a clear diagnostic assessment. Thus, for example, there exist isoenzymes of the muscle (M) and heart (H) type of lactate dehydrogenase (LDH) of which only the H4 type permits an assessment regarding the course of a heart infarct. In the case of creatine kinase (CK), isoenzymes of the muscle (MM), brain (BB) and heart (MB) type are known but only the CK-MB variant is relevant for heart diagnosis. α-Amylase exists as the pancreatic (P) and salivary (S) type, P-α-amylase being important for the diagnosis of the pancreas.

Immune tests frequently do not permit the use of per se suitable labelling enzymes for the investigation of undiluted samples because endogenic enzymes, i.e. enzymes present in the sample liquid to be investigated, display an isoenzymatic activity. Thus, in blood samples endogenic alkaline phosphatase and peroxidase activities exist which do not permit the use of corresponding isoenzymatic labelling enzymes. Also for β-galactosidase from *Escherichia coli*, which is often used as a labelling enzyme, there is an isoenzyme in body fluids which disturbs especially in the case of the use of substrates with a low pK value.

For the detection of an enzyme from the isoenzyme mixture, there are particular reaction mixtures which, to a certain extent, are successful. In published European Patent Application No. 0,150,309, it is suggested, for the determination of pancreatic amylase in the presence of salivary amylase, to precipitate the salivary isoenzyme by means of antibodies and to separate off or to remove the salivary isoenzyme from the sample by means of fixed antibodies. In both cases, a separation step is necessary, which complicates the analysis. The expenditure of time for the determination of pancreatic amylase in the presence of salivary amylase according to this process amounts to about half an hour, especially because of the time-consuming incubation of the sample with the inhibiting antibodies.

Clinical Chemistry, 28, 1525-1527/1982 describes a process in which, for the determination of pancreatic amylase in the presence of salivary amylase, the disturbing salivary enzyme is inactivated by means of an inhibitor isolated from wheat germs. This admittedly permits a measurement in homogeneous solution but, for solutions with high amylase activity, a dilution is recommended before the determination. Furthermore, the selectivity is unsatisfactory. Also in the case of the optimum inhibitor concentration, about 13% of the activity of the salivary enzyme is retained, whereas the activity of the pancreatic enzyme is reduced to about 81%. The expenditure of time for carrying out the process described in this cited literature reference is about 10 to 15 minutes, 5 minutes of which are employed for the inhibition of the salivary enzyme.

Federal Republic of Germany Patent Specification No. 35 00 526 describes mono clonal antibodies which, in homogeneous solution, inhibit salivary amylase and leave pancreatic amylase unaffected. For carrying out the process for the determination of pancreatic amylase in the presence of salivary amylase, the sample liquid is incubated with the antibody inhibiting the salivary enzyme and thereafter the remaining amylase activity is measured. The period of the incubation for the inhibition of the disturbing isoenzymes is from 15 to 30 minutes.

In published Federal Republic of Germany Patent Specification No. 35 25 926, it is described that, for the determination of pancreatic amylase in the presence of salivary amylase, after inhibition of the salivary isoenzyme by monoclonal antibodies, the necessary incubation time for the inhibition can be substantially reduced when, for the inhibition of the salivary amylase, two antibodies are used, the first of which alone achieves an inhibition of less than 93% and the second antibody admittedly binds to the enzyme but only achieves an inhibition of less than 5%. The incubation time for inhibiting salivary amylase can thus be shortened to about 5 minutes.

The above-mentioned literature references exclusively describe wet tests which are those processes in which the sample is brought into contact with solutions or suspensions of the required reagents in a cuvette, a test tube or an appropriate liquid container. The precisely measured addition of reagents to the sample to be investigated and further possibly necessary steps require trained investigation personnel and are, therefore, personnel- and time-intensive because of the operations necessary during the determination procedure. In contradistinction thereto, carrier-bound tests contain all the reagents necessary for carrying out a process on a solid carrier so arranged that, after application of the sample to be investigated to the carrier, no further manipulations by the investigating personnel on the sample liquid are necessary. Clinical Chemistry, 31, 1000/1985 gives an example for a carrier-bound isoenzyme test. A thin film element is there described with which creatine kinase B can be determined in the presence of creatine kinase M. The process depends upon the inhibition of the disturbing isoenzyme creatine kinase M by appropriate antibodies and measurement of the remaining creatine kinase activity which is to be associated with the creatine kinase B. The reagents needed for the determination process are present on the test carrier and come into contact with the liquid sample after application thereof to the test carrier. The creatine kinase isoenzyme test requires an incubation time of 7 minutes for inhibiting the disturbing isoenzyme and cannot be carried out with whole blood.

An optimised version of this carrier-bound isoenzyme test is described in Clinical Chemistry, 32, 1130/1986. By optimisation of the concentrations of the reagents needed for the determination process, it is possible to reduce the incubation time for inhibiting the disturbing isoenzyme to 3.5 minutes. In all, for the determination of the enzyme of interest, more than 5 minutes are needed.

As the prior art shows, processes are known for the determination of an enzyme from an isoenzyme mixture in a liquid sample inhibiting the disturbing isoenzymes and determining the non-inhibited enzyme. However, they suffer from disadvantages since, in part, they require a separation of a sample component, for example of the disturbing isoenzyme, and are not applicable to undiluted samples with a high amylase activity or for whole blood. A general disadvantage of the processes of the prior art is that, for the inhibition of the disturbing isoenzyme, considerable incubation times are necessary before the actual determination reaction can be carried out. Hitherto, no isoenzyme test has been known which is concluded in less than 5 minutes. However, precisely for modern medical diagnosis, it is an aim to carry out determinations as quickly as possible, be it in order to make the urgently necessary decisions for the treatment of emergency cases or in order to diagnose a patient within a physician's consultancy period so as to be able to initiate the appropriate therapy.

Therefore, it is an object of the present invention to provide a possibility for determining an enzyme from an isoenzyme mixture as quickly as possible but in any case in less than 5 minutes. The determination should not require any separate separation step for the isoenzyme and should be capable of being carried out as universally as possible with undiluted liquid samples, especially body fluids, such as urine, saliva, liquor, duodenal juice and preferably also blood plasma, blood serum and whole blood. Whole blood, plasma and serum samples should provide comparable results. Furthermore, the isoenzyme determination should be capable of being carried out with the smallest possible amounts of sample.

Thus, according to the present invention, there is provided a process for the determination of an enzyme from an isoenzyme mixture in a liquid sample by inhibition of the disturbing isoenzymes and determination of the non-inhibited enzyme, wherein the isoenzyme mixture is contacted with one or more substances which are able to inhibit the disturbing isoenzymes, the sample containing the inhibiting substance(s) is transferred to a small-pored reaction medium and the disturbing enzyme is there inhibited and the determination of the non-inhibited enzyme is carried out in the resulting liquid.

Furthermore, the present invention provides a test carrier for the rapid determination of an enzyme from an isoenzyme mixture in a liquid sample by inhibition of the disturbing isoenzymes and determination of the non-inhibited enzyme, said test carrier containing a sample application region and an evaluation region, as well as several test layers, wherein, in the sample application region, a large-pored material contains one or more substances which are able to inhibit the disturbing isoenzymes, a small-pored reaction medium is in direct contact thereto making possible a liquid transport from the large-pored material and in the evaluation region are arranged one or more layers which contain the substances necessary for the determination of the non-inhibited enzyme by means of a characteristic signal and which are in contact with the small-pored reaction medium making possible a liquid transfer or which can be brought into such a contact with this.

The object of the present invention is especially solved by the use of an above-described test carrier for the determination of an enzyme from an isoenzyme mixture in a liquid sample.

The present invention depends essentially on the fact that we have, surprisingly, found that a very rapid determination of an enzyme from an isoenzyme mixture in a liquid sample is possible by inhibition of disturbing isoenzymes and determination of the non-inhibited enzyme when a liquid sample (by which is also to be understood a liquid derived from the sample) is mixed with the substance(s) directed against the disturbing isoenzymes and the liquid containing this substance or these substances is then transferred into a small-pored reaction medium where the inhibition of the disturbing isoenzymes essentially takes place. The inhibition is concluded within a very short period of time of the order of less than one minute. Subsequently, the determination of the non-inhibited enzyme can take place in known manner.

As liquid sample, there can, in principle, be used any liquid containing the enzyme to be determined in an isoenzyme mixture. Preferred are body fluids, such as blood, plasma, serum, urine, liquor, saliva or duodenal juice, blood, plasma and serum being quite especially preferred. When using whole blood, in most cases it is recommended to remove cellular blood components, especially erythrocytes, before contacting the sample with substances directed against disturbing isoenzymes. When body fluids are to be investigated, they do not have to be diluted for carrying out the process according to the present invention.

By inhibition is to be understood the complete inhibition of an enzyme activity. According to the present invention, by a complete inhibition is to be understood an inhibition of more than 90% and preferably of more than 95%. This means the isoenzyme to be inhibited must, after inhibition, display less than 10% and preferably less than 5% of residual activity.

For the process according to the present invention, all substances can be used for inhibiting isoenzymes which fulfil the above-mentioned conditions and which, furthermore, do not substantially influence the activity of the enzyme to be determined. The cross-reactivity of substances inhibiting the disturbing isoenzymes with the enzyme to be determined should advantageously be less than 5%. Furthermore, the inhibiting substances to be used for the process according to the present invention should not negatively influence the determination of the non-inhibited enzyme.

In principle, for the process according to the present invention, all inhibiting substances can be used which fulfil the above-given conditions. Antibodies against the disturbing isoenzymes having proved to be especially useful. Monoclonal antibodies have a quite specific inhibiting action. Such antibodies have already been described or the production thereof is known. For the determination process according to the present invention, antibodies as such or the corresponding fragments thereof displaying inhibiting properties can be used. Therefore, the term "antibodies" is here also to be understood to include such fragments.

From published Federal Republic of Germany Patent Specification No. 35 00 526 are known monoclonal antibodies which specifically inhibit salivary α-amylase. Such antibodies have been deposited at the NCACC (National Collection of Animal Cell Cultures, Porton Down, GB) under the numbers (99D12) 84122003 and (89E2) 84122004. Such antibodies can be advantageously used for determining pancreatic α-amylase in the presence of salivary α-amylase by the process according to the present invention. The same applies to the combination of two antibodies against salivary α-amylase described in published Federal Republic of Germany Patent Specification No. 35 25 926. Such antibodies have been deposited at the NCACC (National Collection of Animal Cell Cultures, Porton Down, GB) under the numbers (99D12) 84122003 and (89E2) 84122004, as well as 84111301 and 84111302. Especially the combination of the monoclonal antibodies directed against salivary α-amylase with the deposit numbers 84122003 and 84111301 or 84122004 and 84111301 has proved to be outstandingly useful for the process according to the present invention for the determination of pancreatic α-amylase in the presence of salivary α-amylase.

For the process according to the present invention, it is necessary that the isoenzyme mixture is contacted with inhibiting substances directed against the disturbing isoenzymes. This is to be understood to mean that the substances are added to the isoenzyme mixture or vice versa. It is advantageous when the isoenzyme mixture is added to the inhibiting substance and takes this up in such a manner that a homogeneous medium is formed. Homogeneous medium means that the substance is present in intimate admixture with the isoenzyme mixture. After contacting by the isoenzyme mixture, the substance is advantageously dissolved in the liquid of the sample.

The inhibition of the disturbing isoenzyme can, in part, already take place during the contacting of the isoenzyme mixture with the inhibiting substance. In order to achieve a rapid and complete inhibition, the sample containing the inhibiting substance must, however, be transferred as quickly as possible into a small-pored reaction medium where the inhibition takes place quickly and completely. Advantageously, the sample is introduced into the small-pored reaction medium within less than one minute, preferably within a few seconds, after contacting with the inhibiting substance. Disturbing enzymes are there inhibited in a very short time, as a rule in one minute or less.

The determination of the remaining enzyme activity, which corresponds to the activity of the enzyme to be determined, can then take place by addition of the necessary reagents within the small-pored reaction medium or the sample can be removed from the small-pored reaction medium and investigated outside of this material for the enzyme to be determined. The determination of the non-inhibited enzyme takes place by means of known substrates according to known methods. For the determination of pancreatic α-amylase, there can, for example, be correspondingly carried out the processes described, for example, in published Federal Republic of Germany Patent Specifications Nos. 35 00 526 and 35 25 926, published European Patent Specification No. 0 150 309 and Fresenius, Z. Anal. Chem., 324, 304–305/1986.

The process according to the present invention can be carried out especially quickly and advantageously in carrier-bound form. Carrier-bound means that all the reagents and materials necessary for carrying out the process are arranged on an inert carrier and preferably an inert synthetic material. The carrier-bound carrying out of the process makes possible a very rapid determination of the desired enzyme even with very small amounts of sample.

For the process according to the present invention, especially in carrier-bound form, the substance inhibiting disturbing isoenzymes is so applied to a large-pored material that it is dissolved off in the case of contact with the liquid sample. The isoenzyme mixture is applied to this so-loaded large-pored material and the inhibiting substance is dissolved off. By means of physical forces, for example gravity or capillary forces but preferably by capillary forces, the liquid containing the inhibiting substance is then transferred into the small-pored reaction medium. This can take place indirectly via another material but advantageously directly by a contact between large- and small-pored material making possible a direct liquid transport.

Large-pored materials in the meaning of the present invention are, in principle, all materials which have such a large surface area that an amount of inhibiting substance sufficient for the process according to the present invention can be applied and this can rapidly be dissolved off in the case of contact with liquid and which makes possible a rapid passing through of liquid. The dissolving off of the inhibitor from the large-pored material and the liquid transport in the small-pored reaction medium must not represent a velocity-determining step of the determination process. There are preferably used fleece or fabrics of monofilar or multifilar woven type of swellable or non-swellable material. Because of their smaller liquid retention capacity, which is very important especially in the case of the investigation of small amounts of sample, non-swellable materials are especially preferably used. By liquid retention capacity is understood that amount of liquid which cannot be sucked out of the large-pored material by the suction force of the small-pored material and remains there. Preferably, the liquid retention capacity should be less than 20% and especially preferably less than 10% of the sample volume used. Appropriate large-pored materials are preferably made of polyester. Nylon fabrics or mixed fabrics of nylon and polyester can also be used. Especially preferred are large-pored materials with an air passage, referred to the pore size, of more than 2000 l./m² sec. We have found that below this air passage limit, the sample passage through the large-pored material no longer takes place quickly enough as is necessary according to the present invention but rather that the liquid transport through this material and from this material becomes the speed-determining step. The large-pored material is preferably a fabric with a thickness of from 70 to 140 $\mu$m. and an air passage of from 2000 to 10000 l./m² sec. and especially those fabrics with a thickness of from 85 to 105 $\mu$m. and from 4000 to 7000 l./m² sec. air passage. Single filament endless fleece of comparable thickness and pore width can also be used.

The small-pored reaction medium in the meaning of the present invention is a material the surface of which is wettable by the liquid sample to be investigated and which possesses pores smaller than 25 $\mu$m., preferably with a size of from 0.5 to 25 $\mu$m. and especially preferably of from 1 to 10 $\mu$m. The lower limit of the pore size is determined by the viscosity of the undiluted usable samples, especially those of blood, plasma or serum. If this lower limit is gone below, the complete take-up of the sample into the small-pored reaction medium becomes the rate-determining step of the determination process. Since, as we have found, the inhibition of disturbing enzymes takes place substantially more quickly within the small-pored reaction medium than on the outer surface of the reaction medium or without such a small-pored material, the sample liquid must be able to penetrate as quickly as possible into the small pores. The pore upper limit is given by the fact that, above this pore size, because of the smaller capillary forces, the take-up speed of the sample is also so low that materials with pores above this limit no longer permit the achievement of the object according to the present invention.

For the process according to the present invention, the absorbent capacity of the small-pored reaction medium should be from 5 to 100 $\mu$l./cm². The thickness of the material can be from 80 to 1000 $\mu$m.

For the preferred case that the determination of the non-inhibited enzyme is not to take place in the small-pored medium but rather in another reaction medium, compressable materials are especially advantageous as small-pored reaction medium. The liquid to be investigated for its residual activity can then easily be transferred from the small-pored reaction medium into another material by pressing the latter on to the former so that, by means of this pressure, a contact is produced making possible a liquid transport. The liquid transport is essentially brought about by physical forces, such as gravity and/or capillary forces.

Not only for the large-pored material but also for the small-pored material which are used in the process according to the present invention, it is important that it does not enter into any bondings, either of an adsorptive or of a chemical nature, with sample component materials. In this connection, by sample component materials are understood not only the substances originally contained in the sample to be investigated but also substances and reagents which get into the sample during the determination process. Undesired bindings can give rise to falsified measurement results. Materials which, as such, would, in this sense, enter into bindings with sample component materials, can possibly be so treated that they lose the undesired property of non-specific binding of sample component materials. Materials treated in this manner can then also be used for the process according to the present invention as small-pored or large-pored materials. Measures for the suppression of undesired non-specific bindings of sample component materials to solid materials are well known from the prior art. For example, the undesired non-specific binding of sample proteins to the test carrier materials can be overcome by treating these materials with albumin.

Advantageously preferred as small-pored reaction media are fabrics, fleece, membranes and films which possess the above-given properties.

Materials which can be used for the small-pored reaction medium are membranes, the surfaces of which are possibly so modified that no undesired binding of sample component materials takes place in the above-mentioned sense. Such materials, which are commercially available, include, for example, Loprodyne ® of Pall, Glengrove, New York, U.S.A. and hydrophilic Durapore ® of Millipore, Bedford, U.S.A. Cellulose and cellulose derivative membranes saturated by means of inert proteins, for example albumin, can also be used. Cellulose derivatives include, for example, cellulose esters, cellulose ethers and nitrocellulose. Nylon membranes treated against non-specific binding can also be used as small-pored reaction media in the process according to the present invention.

Also advantageously usable are films which are porous possibly because of the presence of corresponding component materials, for example kieselguhr. Such so-called open films are described, for example, in published European Patent Specification No. 0,016,387.

Fleece based on viscose staple fibre, glass fibres or synthetic materials, such as nylon, polyester and polyethylene, can also be advantageously used.

Especially preferred as small-pored reaction medium are membranes with pores of from 3 to 7 $\mu$m. and especially of about 5 $\mu$m., and glass fibre fleece with pores of from 1 to 10 $\mu$m. and especially of from 1 to 5 $\mu$m.

For the carrying out of the process according to the present invention in carrier-bound form, it has proved to be especially advantageous when the pore size ratio of the large-pored material to the small-pored reaction medium is from 2 to 2000, preferably from 5 to 500 and quite especially preferably from 10 to 100.

For carrying out the process according to the present invention in carrier-bound form, a test carrier can be used which contains a sample application region and an evaluation region, as well as several test layers. Test carriers are frequently formed as longitudinal test strips. However, test carriers are also known which are made as quadratic or rectangular platelets. Test carriers consist essentially of test layers, i.e. materials which contain the reagents necessary for the test to be carried out. However, as in the present case, test layers can participate in the construction of the test carrier which carry no reagents but rather which, for example, on the basis of their material structure, transport the liquid to be investigated from one test layer to another which, as reaction medium, quasi like a reaction vessel, takes up substances reacting with one another or which acts as a filter for certain sample component materials.

Test carriers in general and especially also according to the present invention can be divided up into a sample application region and an evaluation region. The sample application region is the zone of the test carrier to which the sample is applied. The evaluation region is the zone where, as a result of the investigation, a signal is measured which is a measure for the parameter to be determined. The sample application region and the evaluation region are mostly not identical but rather, as also in the case of the present invention, are connected with one another by a medium making possible a liquid transport.

The test carrier according to the present invention contains, in the sample application region, large-pored material of the previously described type which contains one or more substances as were previously mentioned and which are able to inhibit isoenzymes which disturb the determination of an enzyme from an isoenzyme mixture. Subsequent thereto, a small-pored material of the previously described type, which serves as a reaction medium, is so arranged that it is in contact with the large-pored material making possible a liquid transport therefrom. The small-pored material connects the sample application region and the evaluation region of the test carrier according to the present invention and thus, besides its function as a reaction medium for inhibiting disturbing isoenzymes, also serves for the transport of the liquid sample to be investigated from the sample application region into the evaluation region.

The evaluation region of the test carrier according to the present invention contains one or more signal-forming layers. The signal-forming layers contain the reagents necessary for the determination of the non-inhibited enzyme and are so arranged that they are in contact with the small-pored reaction medium making possible a liquid transfer or can be brought into such a contact therewith. Preferably, not only with the contact between the signal-forming layers and the small-pored reaction medium but also with the contact between the small-pored reaction medium and the large-pored inhibitor carrier is, in each case, meant a laminar contact so that a contact surface which is as large as possible is produced.

In the case of contact of the liquid to be investigated with the detection reagents of the signal-forming layers, a detectable signal is produced which represents a measure for the amount of the non-inhibited enzyme. The present invention is concerned especially with those cases in which, as detectable signal, a characteristic colour change is produced, a colour formation thereby also being regarded as a colour change (from colourless to coloured). As reagents for the determination of the non-inhibited enzyme from an isoenzyme mixture, there can be used those previously mentioned for the determination process.

If the reagents necessary for the signal-forming reaction are compatible with one another and do not have a negative influence, for example with regard to their stability, then the reagents can be present together in one layer. However, it can possibly be necessary spatially to separate the determination reagents and to provide them on several layers. In this case, there are then several signal-forming layers which only in total contain all of the reagents necessary for the determination reaction.

One embodiment of a preferred test carrier according to the present invention contains these signal-forming layers so arranged that they either stand full-facedly in contact with one another or can so be brought into contact with one another. Such a contact must have the result that liquid can pass over from one layer into the other.

If the reagents necessary for the determination reaction are contained in several signal-forming layers, all must be in contact with the small-pored reaction medium making possible a liquid transfer or can be brought into such a contact therewith. In a preferred embodiment of the test carrier according to the present invention, only one of several layers each containing parts of the determination reagents is in direct contact with the small-pored material or can be brought into direct contact therewith. The other layers containing the remainder of the reagents necessary for the determination reaction are above this previously-mentioned layer in indirect contact with the small-pored reaction medium or can be brought into such an indirect contact therewith. Indirect contact here means that these layers have no direct contact making possible a liquid transfer but rather liquid can only pass over via a layer lying therebetween.

A signal-forming layer of the test carrier according to the present invention consists of a material which carries all or a part of the reagents necessary for the determination of the non-inhibited enzyme. This reagent carrier material can, in principle, be selected from all materials usually employed for this purpose. They can be, for example, absorbent or swellable, porous or non-porous materials or there can also be used those which, in the case of contact with the liquid to be investigated, dissolve therein. By way of example, there may be mentioned cellulose, filter paper, synthetic material or glass fibre fleece, polyvinyl esters and polyamide films, as well as films of, for example, xanthan gum. Absorbent, swellable and/or porous materials are preferred which ensure a good liquid transfer from the small-pored reaction medium into the signal-forming layer(s).

The signal produced in the signal-forming layer or layers can, in the case of a colour change, be determined not only visually but also photometrically, a reflection-photometric measurement of the signal produced being especially preferred.

When the test carrier according to the present invention is to be used for the determination of an enzyme from an isoenzyme mixture in blood, it advantageously has, in the sample application region, a layer for the separation of cellular components from blood. Porous layers such as are known, for example, from published European Patent Specification No. 0,045,476 are especially advantageously used. The separation layer is so arranged in the test carrier according to the present invention that the sample to be investigated first contacts the large-pored layer after passage through this separation layer.

The advantage of the present invention is, in particular, to be seen in the fact that it is possible for the first time to determine an enzyme from an isoenzyme mixture in less than 5 minutes and preferably even in less than 3 minutes. This is, in particular, achieved in that disturbing isoenzymes are inhibited very quickly, preferably in one minute or less, in the small-pored reaction medium used according to the present invention. Furthermore, for an enzyme determination according to the present invention, no separate separation step is necessary for disturbing isoenzymes. In general, undiluted liquid samples, especially body fluids, can be investigated and it is especially advantageously to be stressed that blood and plasma or serum samples provide comparable results. Finally, especially in the case of the use of test carriers according to the present invention, amounts of sample of 30 µl. or less suffice for the determination of the desired enzyme.

The present invention will now be explained in more detail in the following, with reference to the embodiments illustrated schematically in the accompanying drawings, in which:

FIGS. 1, 2 and 3 show cross-sections through different embodiments of test carriers according to the present invention; and FIG. 4 shows a side view of a preferred embodiment of a test carrier according to the present invention.

FIG. 1 shows in cross-section a test carrier in which all the test layers are in contact making possible a liquid transfer, the test layers being held together by a frame (8). The frame (8) can consist of the most varied materials. It only has to fulfil the task of holding the test layers together. There can be used, for example, a melt adhesive strip or also a paperboard frame, such as is known, for example, from photographic diapositives.

The sample application region consists of layers (1) and (2). (1) is a layer for the separation of cellular components from blood, especially of erythrocytes. This blood cell separation layer makes it possible to carry out the process according to the present invention for the determination of an enzyme from an isoenzyme mixture in whole blood without previously having to remove the blood cells separately. As material for the blood cell separation layer, there can, in principle, be used all materials known for this purpose. However, it is especially preferred to use glass fibre fleece, such as are described in published European Patent Specification No. 0,045,476. If whole blood samples are not to be investigated with the test carrier according to the present invention but rather only samples which do not require the removal of cellular components, then a separation layer is also not necessary. In order to ensure a uniform wetting of the test layers of the test carrier over the whole of their surface, it is, however, recommended to arrange over the remaining test layers a layer (1) which is able to spread the applied sample liquid even when no cellular sample components are to be separated off. Appropriate materials for such spreading layers are known from the prior art. A glass fibre fleece according to published European Patent Specification No. 0,045,476 brings about not only a separation of cellular blood components but also a uniform wetting of the underlying test layers over the whole of their surface. (2) is a layer of large-pored material which contains the substance inhibiting the disturbing isoenzymes and (3) is the small-pored reaction medium in which the disturbing isoenzymes are inhibited. (4) is a signal-forming layer which contains the reagents necessary for the determination of the non-inhibited-enzyme and represents the evaluation region of the test carrier.

When using the test carrier of FIG. 1 for the determination of an enzyme in an isoenzyme mixture, the liquid sample to be investigated is applied to the layer (1) where a uniform distribution on the whole of the surface of the test layer takes place. When the sample to be investigated is whole blood, layer (1) is a material which, furthermore, is able to separate off cellular blood components. The liquid passes due to large-pored layer (2), where it dissolves off the substance inhibiting the disturbing isoenzyme. The liquid mixed with this substance is sucked up very quickly into the small-pored reaction medium (3). For a quantitative determination of the sample, it is necessary that the liquid retention capacity of the layer (2) is as small as possible. In layer (3) there takes place the inhibition of the isoenzymes disturbing the determination of the desired enzyme before the liquid reaches the signal-forming layer and there produces a signal which represents a measure for the amount of enzyme to be determined in the sample. A colour change in the signal-forming layer is preferably caused by the enzyme to be determined. This colour change can be measured on the side of the layer 4 remote from the sample application side visually or photometrically and especially preferably reflection photometrically.

FIG. 2 differs from FIG. 1 in that the illustrated embodiment of the test carrier according to the present invention does not contain all of the reagents necessary for the determination of the enzyme to be measured in a single signal-forming layer. On the contrary, the reagents are here divided on layers (5) and (6) which together represent the evaluation region. Thus, reagents which are incompatible with one another can be spatially separated from one another in an advantageous manner. The liquid to be investigated takes up, upon its passage through the layer (5), the reagents necessary for a reaction with reagents of layer (6) or the first reaction steps of a reaction sequence take place in layer (5) with the reagents there present, the reaction sequence then being completed with the reagents present in the layer (6).

In FIG. 3, the evaluation region is formed like a flap, layers (5) and (6) containing the reagents necessary for the determination reaction in spatially separated form. For a better handling, layer (6) is applied to a transparent film (7) which is inert for the determination reaction and is connected with the frame (8) by means of a movable hinge-like element (9). With the help of the flap-like arrangement of the layers (5) and (6), it is possible to start a chronologically precisely defined determination reaction. If, after sample application, the liquid has penetrated through to the layer (5) and has dissolved the reagents there present or if it has entered with the reagents present therein into the first reaction step of a reaction sequence consisting of several reaction steps, then, at a definite point of time, by closing the flap, the layer (6) is brought into contact with the layer (5) and the liquid passes over into this layer. The determination reaction is brought to completion and can be observed visually or photometrically over a definite, known period of time through the transparent film (7).

FIG. 4 shows a preferred embodiment of a test carrier in strip form. On a stiff base film (10) are fixed the test layers necessary for the determination with melt adhesive strips (11) and (20). In sample application region (18) are arranged, under a covering mesh (12) of synthetic material, preferably polyester, a fleece for separating off cellular components from blood (13), preferably a glass fibre fleece, and a large-pored inhibitor carrier (14). A small-pored reaction medium (15) is in contact with the inhibitor carrier (14), making possible a liquid transfer, and extends, lying on the base film (10), from the sample application region (18) into evaluation region (19). Signal-forming layers (16) and (17) are so fixed with a melt adhesive strip (20) on to the stiff base film (10) that they are present in the evaluation region but do not contact the small-pored reaction medium (15).

For carrying out the process according to the present invention by means of the test carrier of FIG. 4, a liquid sample, for example whole blood, is applied to the covering mesh (12). The liquid sample passes through the covering mesh into layer (13) where, in the case of the use of whole blood as sample, cellular blood components are held back. On the basis of gravity and of capillary forces, the sample passes into the inhibitor carrier (14) where the substance inhibiting the disturbing isoenzyme is dissolved off. The sample with the inhibitor is sucked very quickly into the small-pored reaction medium (15), where the inhibition takes place very quickly. Due to capillary forces, the sample in the small-pored reaction medium is transported from the sample application region (18) into the evaluation region (19). After conclusion of the inhibition of disturbing isoenzymes, the layers (16) and (17) provided for the determination of the non-inhibited enzyme are so pressed on to the small-pored reaction medium (15) that the reagents present in these layers come into contact with the liquid to be investigated. A colour change occurring in layer (17) as a measure for the amount of enzyme in the sample to be determined can be measured visually or photometrically and preferably reflection photometrically in this layer from the side lying opposite the base film (10).

It is self-evident that the dimensions of the test carrier and especially the dimensions of the individual test layers must be adapted to the sample volumes to be investigated.

The following Examples are given for the purpose of illustrating the present invention. Nevertheless the examples should not represent a restriction of the matter of present invention:

EXAMPLE 1

Comparison of Various Test Carriers With Different Material Combinations for Inhibitor Carrier and Small-Pored Reaction Medium

A) Production of the Test Carrier

Four test carriers according to FIG. 4 are produced in which the inhibitor carrier (14) in the case of model 1 consists of polyester fabric multi 14 normal with a pore size of 100 μm. (Schweizer Seidengazefabrik, Thal, Switzerland), in the case of model 2 also of polyester fabric multi 14 normal with a pore size of 100 μm. (Schweizet Seidengazefabrik, Thal, Switzerland), in the case of model 3 of long fibre paper with a surface weight of about 17 g./m² and a pore size of from about 50-300 μm. (Schöller Hösch, Federal Republic of Germany) and in the case of model 4 of a nylon membrane with a pore size of 1.2 μm. (Pall, Glengrove, New York, U.S.A.), these materials being, in each case, impregnated with an aqueous solution which contains the following components:

- 100 mM phosphate buffer (pH 7.0)
- 50 mM sodium chloride
- 1 wt. % crotein C (Croda, Cheshire, Great Britain) and so many mg./ml. of anti-salivary amylase antibody of the deposit numbers 84122004 and 84111301 in the ratio of 5:1 that there is provided an amount of about 10 to 12 μg. of antibody/cm² of fabric.

The small-pored reaction medium (15) consists, in model 1, of a glass fibre fleece of the firm Binzer (Hatzfeld, Federal Republic of Germany) with a pore size of about 1 to 5 μm., in model 2 of a nylon membrane with a pore size of 0.45 μm. (Pall, Glengrove, New York, U.S.A.), in model 3 of a glass fibre fleece of the firm Binzer (Hatzfeld, Federal Republic of Germany) with a pore size of about 1 to 5 μm. and in model 4 also of a glass fibre fleece of the firm Binzer (Hatzfeld, Federal Republic of Germany), with a pore size of about 1 to 5 μm.

In the case of all of the models, the signal-forming layer (16) consists of a polyamide fabric (NY20HC, Zürcher Beuteltuchfabrik, Zurich, Switzerland) which was impregnated with the following aqueous solution:

- 5.8 g./litre 2-methoxy-4-morpholinobenzenediazonium chloride x zinc chloride and
- 20% by weight methanol, so that there was provided an amount of about 15.5 μg./cm² of diazonium salt.

Layer (17) is a reagent film on a film of synthetic material. The film is so produced that a solution of:

- 3 g. Keltrol ®F (Kelco, Dreieich, Federal Republic of Germany)
- 15.5 g. sodium phosphate for phosphate buffer (pH 7.0)
- 0.6 g. sodium chloride
- 1 MU α-glucosidase and
- 25 g. indoxymaltoheptaoside (Boehringer Mannheim GmbH, Mannheim, Federal Republic of Germany)

in 1 litre of water is coated at a temperature of from 0° to 4° C. on to a polycarbonate film of the firm Lonza, Weyl, Federal Republic of Germany, so that there is obtained an amount of 6 U/cm² of enzyme and 140 μg./cm² of indicator.

As erythrocyte separation fleece (13), for all four models, there is used a glass fibre fleece of the firm Binzer (Hatzfeld, Federal Republic of Germany) with a pore size of 5-25 μm. A polyester mesh (12) (Zürcher Beuteltuchfabrik, Zürich, Switzerland) is also used for all four models. The polyester mesh (12) and the erythrocyte separation fleece (13) are cut up into 6×6 mm.-sized pieces, the inhibitor carrier (14) into 6×7 mm.-sized pieces, the small-pored reaction medium (15) into 16×6 mm.-sized pieces and the signal-formation layers (16) and (17) into 13×6 mm.-sized pieces, arranged as shown in FIG. 4 and fixed with melt adhesive strips on to a stiff polystyrene film with a size of 100×6 mm. as base layer (10).

B) Carrying Out of the Determination Process

Blood and serum samples from a donor contain 42 U/litre of pancreatic α-amylase. The samples are made up with salivary amylase to a total of 8500 U/litre salivary α-amylase. In each case, 30 μl. of sample are applied to the covering mesh (12) of the individual carriers of models 1 to 4. The test carriers are investigated in a reflection photometer of the type Reflotron ® of the firm Boehringer Mannheim GmbH, Mannheim, Federal Republic of Germany. The test time is, in all, 170 seconds. 1 Minute after sample application, the layers (17) and (16) are pressed on to the reaction medium and the determination reaction of the non-inhibited amylase portion is thus started. The colour formation is monitored reflection photometrically at 567 nm. The following results are obtained:

TABLE 1

| model | salivary α-amylase used in U/l. | measurement value in U/l. | divergence (variation coefficient) | nature of sample |
|---|---|---|---|---|
| 1 | 8500 | 235 | 2.9 | serum |
| 1 | 8500 | 231 | 3.5 | blood |
| 2 | 8500 | 520 | 25.4 | serum |
| 2 | 8500 | — | — | blood |
| 3 | 8500 | 270 | 3.7 | serum |
| 3 | 8500 | 225 | 4.8 | blood |
| 4 | 8500 | 375 | 13.8 | serum |
| 4 | 8500 | — | — | blood |

The results show that only model 1 enables a very good inhibition of the salivary α-amylase to be achieved within a short period of time (more than 97%), a good agreement of the measurement results being obtained for serum and blood. In model 2, the pores of the small-pored reaction medium are clearly so small that the sample can only penetrate in very slowly and the inhibition of the salivary α-amylase has not taken place completely within the test time. With model 3, the inhibition of the salivary α-amylase is good. However, the results for serum and blood samples differ from one another by more than 16%. This is clearly due to the liquid retention capacity of about 30% of the long fibre paper used as large-pored material. In the case of the investigation of same volumes of blood and serum, it is to be taken into account that, in the case of blood, depending upon the haemocrit value, only up to one half of the liquid sample volume used is available for the investigation. In the case of very small volumes, such as were here investigated, the liquid retention capacity of the individual layer materials then plays a great part. In the case of model 4, the small pore size of the inhibitor carrier (15) results in the sample passing only slowly into the small-pored reaction medium and the inhibition does not take place completely during the test time. Especially in the case of blood, only a small amount of liquid passes into the small-pored reaction medium so that the liquid is already dried in during the measurement time and cannot be measured.

EXAMPLE 2

Test Carrier for the Specific Detection of Pancreatic α-amylase

A test carrier is produced according to FIG. 4. The inhibitor carrier (14) is a polyester fabric multi 14 normal (Schweizer Seidengazefabrik, Thal, Switzerland) which is impregnated with the following aqueous solution:
  100 mM phosphate buffer (pH 7.0)
  50 mM sodium chloride
  1% by weight crotein C (Croda, Cheshire, Great Britain)
  2 mg./ml. anti-salivary α-amylase antibody with the deposit numbers 84122004 and 84111301 in the ratio of 5:1 so that there is provided an amount of about 10 to 12 µg. of antibody/cm².

As small-pored reaction medium (15), there is used a glass fibre fleece of the firm Binzer (Hatzfeld, Federal Republic of Germany) with a pore size of about 1 to 5 µm.

The signal-forming layers (16) and (17), the covering mesh (12) and the erythrocyte separation fleece (13) correspond to those described in Example 1.

The individual layers are cut up as described in Example 1 and stuck with melt adhesive strips on to a 100×6 mm.-sized polystyrene film to give a test carrier according to FIG. 4.

To the covering mesh (12) are applied 30 µl. of serum and the test strips evaluated in a Reflotron ® device of the firm Boehringer Mannheim GmbH, Mannheim, Federal Republic of Germany, at a measurement wavelength of 567 nm. One minute after sample application, the signal-forming layers (16) and (17) are pressed on to the small-pored reaction medium (15). The measurement is ended after, in all, 170 seconds from sample application. The following results are obtained:

TABLE 2

| α-amylase activity used | | measurement value for | |
|---|---|---|---|
| pancreatic isoenzyme in U/l. | salivary isoenzyme in U/l. | pancreatic α-amylase in U/ml. | variation coefficient in % |
| 43 | 8366 | 106 | 3.1 |
| 326 | 483 | 334 | 3.5 |
| 1260 | 25 | 1208 | 3.7 |

The measurement values found for pancreatic α-amylase agree very well with the amylase activities used. In the first example, a very large excess of salivary isoenzyme of up to 99% could be inhibited so that the pancreatic value found under these circumstances represented an outstandingly good result.

EXAMPLE 3

Inhibition Efficiency of Salivary Amylase: Comparison to Wet Chemistry

A serum which contained 4250 U/l. salivary amylase was measured comparing the method of the present invention to the commercial available wet chemistry method PNP-Pancreas Amylase (Boehringer Mannheim, FRG) which employs analogous inhibiting antibodies. The test carrier was produced as described in example 2. Measurement was performed as usual after different incubation times with the antibodies on the test strip. Incubation times from 5 sec. to 120 sec. were chosen.

The PNP-Pancreas Amylase method was performed according to the instruction of the manufacturer with the exception of preincubation time, which was varied from 30 to 180 seconds.

The resulting data are summarized in the table:

TABLE 3

| Incubation time in sec. | residual activity by the method of the invention in U/l. | Inhibition in % | residual activity wet chemistry method in U/l. | Inhibition in % |
|---|---|---|---|---|
| 5 | 211 | 95.0 | n.d.* | n.d.* |
| 39 | 134 | 96.9 | 383 | 90.8 |
| 60 | 122 | 97.1 | 207 | 95.1 |
| 120 | 106 | 97.5 | n.d.* | n.d.* |
| 180 | n.d.* | n.d.* | 142 | 96.7 |

*n.d. means "not determined".

The method of invention guarantees inhibition of 95% after 5 sec. of incubation time, and inhibits >97% after 1 minute. The wet chemistry method needs about five to ten times longer (60 sec. and >180 sec.) to show equal inhibition efficiency.

It will be understood that the specification and examples are illustrative but not limitative of the present invention and that other embodiments within the spirit and scope of the invention will suggest themselves to those skilled in the art.

What is claimed is:

1. A process for the determination of a specific isoenzyme present in an isoenzyme mixture such as a body fluid sample, wherein any other isoenzymes present in the mixture are inhibited, and the specific isoenzyme is determined in less than five minutes, with no requisite step for removal of the inhibited isoenzymes, comprising contacting the sample with one or more substances which bind to and are capable of inhibiting all but the specific isoenzyme so that the entire sample remains soluble, transferring the entire sample to a small-pored reaction medium with a pore size less than 25 μm, inhibiting all but the specific isoenzyme while maintaining the entire sample in solution, and carrying out the determination of the specific isoenzyme in the presence of the inhibited isoenzymes which remain in solution.

2. The process of claim 1 comprising inhibiting the other isoenzymes in a large-pored material having an air-passage of more than 2000 $1/m^2 sec^2$ so that the inhibiting substance is dissolved off from the large-pored material.

3. The process of claim 2, comprising contacting the large-pored material directly with the small-pored reaction medium and thereby causing the sample containing the inhibiting substances to be removed from the large-pored material into the small-pored reaction medium.

4. The process of claim 2 comprising contacting the sample wherein the pore size ratio of the large pored material to the small-pored reaction medium is in the range 2:1 to 2000:1.

5. The process of claim 1 comprising contacting the isoenzyme mixture with the small pore reaction medium having pores of the size range of 1–10 μm.

6. The process of claim 1 comprising contacting the isoenzyme mixture with the large-pored material having a liquid retention of less than 20%.

7. The process of claims 1, 2, or 3 comprising inhibiting the other isoenzyme by means of antibody to said isoenzyme.

8. The process of claim 1 comprising inhibiting one or more of the other isoenzymes by greater than 90 or 95%.

9. The process of claims 1, 2 or 3 for the determination of pancreatic α-amylase from a mixture of pancreatic and salivary α-amylase, comprising inhibiting the salivary α-amylase with at least one antibody.

10. The process of claim 9 comprising inhibiting the salivary α-amylase with any two of the monoclonal antibodies selected from the group consisting of 99D12 (84122003), 89E2 (84122004), 84111 301 and 84111 302.

11. The process of claim 1 comprising carrying out the inhibition and determination in carrier-bound form.

12. A flow through test carrier for the determination of a specific isoenzyme present in an isoenzyme mixture in a liquid sample consisting of:

a sample application region and an evaluation region and at least one test layer, wherein the sample application region comprises a large-pored material (A) having an air passage of more than 2000 $1/m^2 sec^2$ and containing one or more substances which bind and inhibit all other isoenzymes without immobilizing them, and a small pored reaction medium (B) with a pore size less than 25 μm, in direct contact with A which facilitates transport of a liquid sample from A to B, where the ratio of pore size A:B is in the range of 2:1 to 2,000:1; and wherein the evaluation region (C) comprises at least one layer containing the test substances necessary for the determination of the specific isoenzyme in the presence of the inhibited, non-immobilized isoenzymes by means of a characteristic test signal and wherein C is in direct contact or can be placed into such contact with B to permit transfer of the liquid sample from B to C.

13. The test carrier of claim 12 wherein the pore size of the small sized medium is 1–10 μm.

14. The test carrier of claim 12 wherein the sample application region contains a first layer for the separation of cellular components from the blood sample and the second large-pored material.

15. The test carrier of claim 12 for the determination of an enzyme present in an isoenzyme mixture in a liquid sample, having contiguous application, reaction and test signal evaluation layers in a frame consisting of a layer for sample spreading or for the separation of cellular components from blood consisting of glass fiber fleece, a layer of large-pored material, a layer of small-pored reaction medium, and a signal forming evaluation layer.

16. The test carrier of claim 15 wherein the evaluation region comprises two layers.

17. The test carrier of claim 16 wherein the two layers are spatially separated.

18. The test carrier of claim 12 wherein the test carrier is in a strip form.

19. The test carrier of claim 12 for the determination of pancreatic α-amylase from a mixture of pancreatic and salivary α-amylase wherein the salivary α-amylase is inhibited with at least one antibody.

20. The test carrier of claim 19 wherein the salivary α-amylase is inhibited with any two of the monoclonal antibodies selected from the group consisting of 99D12 (ECACC 84122003), 89E2 (ECACC 84122004), ECACC 84111301 and ECACC 84111302.

* * * * *

UNITED STATES PATENT AND TRADEMARK OFFICE
CERTIFICATE OF CORRECTION

PATENT NO.  : 5,314,803
DATED       : May 24, 1994
INVENTOR(S) : Hans-Erich Wilk, et al.

It is certified that error appears in the above-indentified patent and that said Letters Patent is hereby corrected as shown below:

Col. 2, line 29:      change "hall" to -- half --.

Col. 13, line 52:     change "Schweizet" to
                      -- Schweizer --.

Signed and Sealed this

Thirteenth Day of December, 1994

Attest:

BRUCE LEHMAN

Attesting Officer          Commissioner of Patents and Trademarks